United States Patent [19]
Rosenberg

[11] Patent Number: 5,178,611
[45] Date of Patent: Jan. 12, 1993

[54] DEVICE AND METHOD FOR INHIBITING INTRAVASCULAR DEVICE ASSOCIATED INFECTION

[76] Inventor: Paul Rosenberg, 1320 York Ave., New York, N.Y. 10021

[21] Appl. No.: 694,109

[22] Filed: May 1, 1991

[51] Int. Cl.⁵ .................... A61M 25/00; A61M 5/00
[52] U.S. Cl. ................................. 604/172; 604/158; 604/265
[58] Field of Search ............... 604/158, 171, 172, 164, 604/264, 265, 280

[56] References Cited

U.S. PATENT DOCUMENTS

| | | | |
|---|---|---|---|
| 4,737,146 | 4/1988 | Amaki et al. | 604/158 |
| 4,846,799 | 7/1989 | Tanaka et al. | 604/158 |
| 4,968,306 | 11/1990 | Huss et al. | 604/264 |
| 5,021,044 | 6/1991 | Sharkawy | 604/164 |
| 5,061,255 | 10/1991 | Greenfeld et al. | 604/265 |

FOREIGN PATENT DOCUMENTS 1403799 10/1975 United Kingdom ............... 604/265

*Primary Examiner*—Paul J. Hirsch
*Attorney, Agent, or Firm*—Cohen, Pontani, Lieberman, Pavane

[57] ABSTRACT

The present invention is directed to a device for reducing the risk of infection associated with the establishment and/or maintenance of intravascular fluid communication between apparatus external to the body and an internal blood vessel. The device includes a first tube capable of penetrating both the layers of skin and tissues surrounding the blood vessel and a wall of the blood vessel, the first tube having a distal end portion operatively insertable into the blood vessel and a proximal end portion operatively disposed outside the blood vessel but within the body. A second tube is disposed within the first tube, the second tube having a distal end portion insertable into the blood vessel through an opening defined at the distal end of the first tube. The first and second tubes define therebetween a longitudinally coaxially disposed channel which establishes a fluid communication path for a first fluid. The first tube has a predeterminately-sized capillary aperture defined in a distal end portion and predeterminately sized so as to predeterminately control the flow of first fluid through the capillary aperture such that as the first fluid is delivered from the channel, outwardly through the aperture, the first fluid remains substantially on and along the outer surface of the first tube so as to coat the outer surface of the first tube with the first fluid, thereby creating an anti-infective barrier which surrounds the intravascular device as it lies beneath the skin and within a blood vessel.

19 Claims, 4 Drawing Sheets

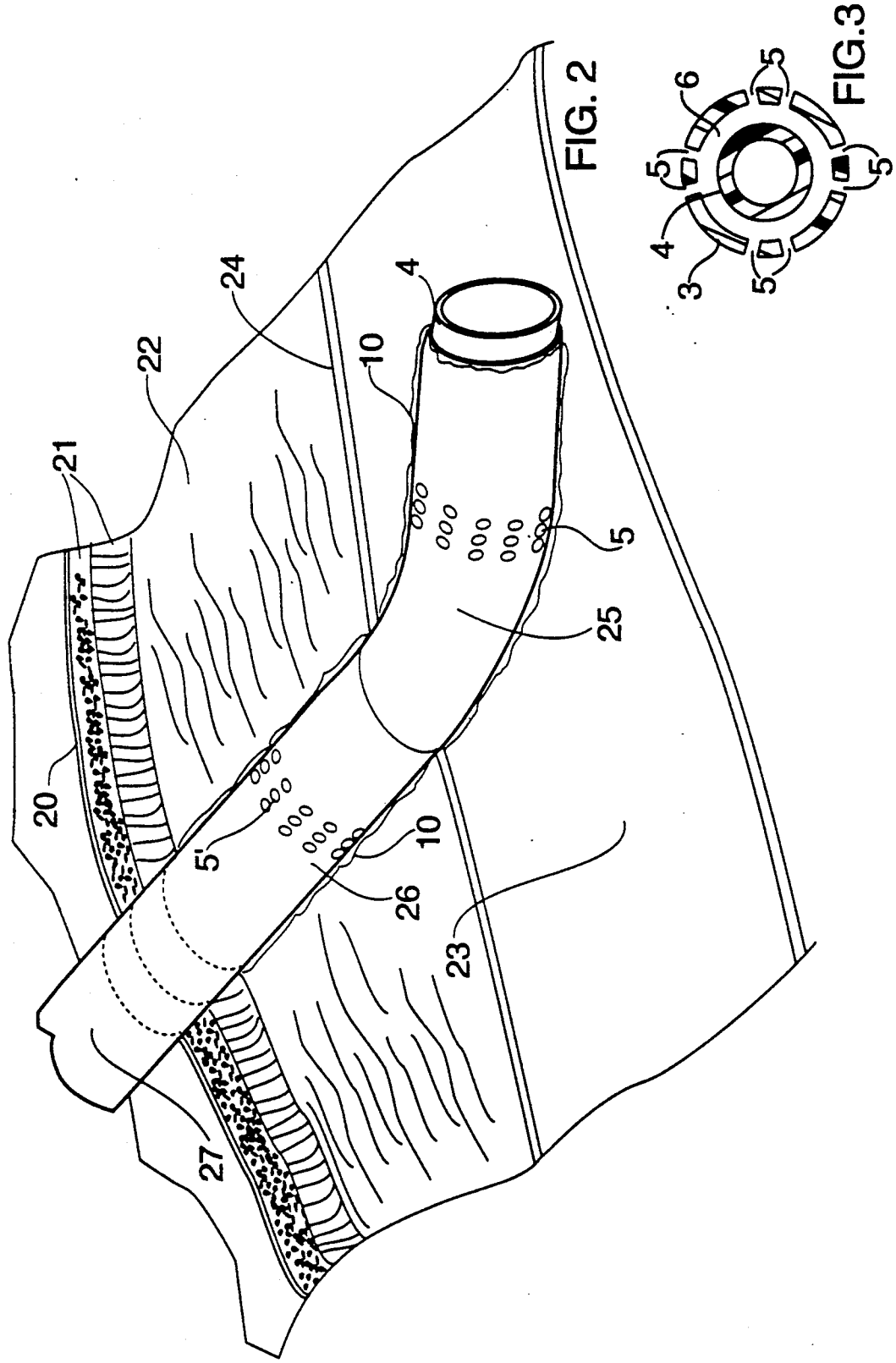

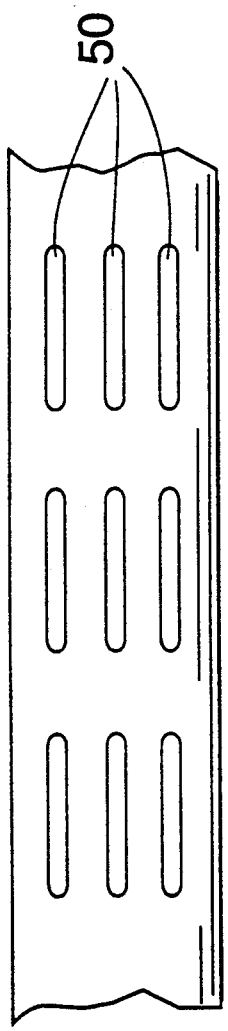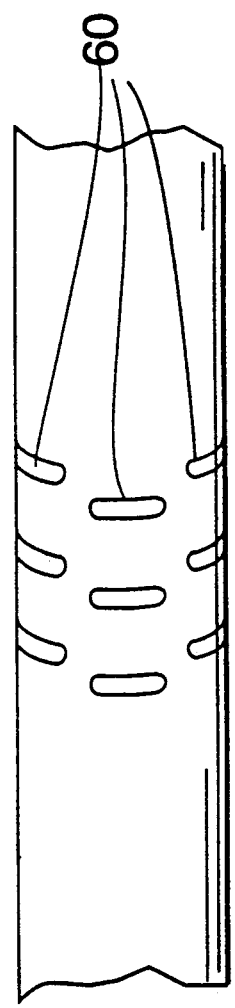
FIG. 5
FIG. 6

DEVICE AND METHOD FOR INHIBITING INTRAVASCULAR DEVICE ASSOCIATED INFECTION

FIELD OF THE INVENTION

The present invention relates to a device for reducing the risk of infection associated with the establishment and/or maintenance of intravascular fluid communication between apparatus external to the body and an internal blood vessel surrounded by layers of skin and tissue.

BACKGROUND OF THE INVENTION

Intravascular devices, such as catheters, are currently used for a variety of medical purposes in a wide range of both diagnostic and therapeutic applications. Catheters are, by way of example, most commonly used in the peripheral blood vessels (i.e. those close to the skin) to support and maintain blood volume levels, to introduce medications into the blood stream, and to provide nutritional support. Catheters are also used in arterial vessels to monitor certain blood parameters and to deliver regional chemotherapy. Connections to veins deep within the body may be established to obtain localized blood samples, to deliver nutritional compounds, to measure cardiac output and, in some cases, may be implanted on a semipermanent basis to deliver chemotherapeutic compounds or to maintain a continuous mode of central venous access.

While the foregoing listing is far from exhaustive, each of these utilities is associated with a substantial risk of infection, particularly where the catheter remains in situ for an extended period of time. While the exact causes of such infections are not completely known, conventional efforts to reduce or eliminate intravascular device-associated infection presently take several forms. The first usually involves pre-insertion cleansing of the skin surface surrounding the area of penetration to prevent contamination of the device as it penetrates the skin by infectious agents which are present on the skin surface. Regular removal and replacement of the intravascular device every two to three days, for example, is also a common anti-infective procedure. Furthermore, different materials such as Teflon (PTFE) and polyvinylchloride (PVC) have been used in the manufacture of catheters, each having demonstrated some ability to prevent the onset of infection by discouraging infectious agents from adhering to and growing on the catheter surface. More recently, catheters have also become available with anti-microbial agents bonded to the exterior surface of the catheter. None of these currently known devices or procedures, however, has proven to be sufficiently effective and successful in preventing the onset of infection on or along those portions of the catheter that extend subcutaneously into the body.

OBJECTS AND SUMMARY OF THE INVENTION

It is accordingly a particular object of the present invention to provide a catheter useful for a variety of conventional intravascular applications while providing a significantly reduced risk of infection over presently known intravascular devices. It is a further object of the invention to provide an intravascular device and method which can be used to reduce the risk of infection not only at the location at which the device resides within the blood vessel but, in addition, at locations remote from the blood vessel such, for example, as at the interface between the catheter peripheral surface and the surrounding body tissue.

The present invention provides, in accordance with the foregoing objects, an intravascular device or catheter comprising, in the embodiment herein disclosed, an outer tube which is inserted through the skin into a blood vessel and an inner tube which is inserted coaxially through the outer tube and also extends into the blood vessel. The inner tube extends beyond the distal termination of the outer tube which sealingly engages the inner tube at the termination of the former. The annular channel formed between the inner and outer tubes provides a fluid communication channel for a first fluid, while the inner tube provides an additional fluid communication path for a second fluid. The first fluid—which may be an anti-microbial agent or the like—is delivered through the channel onto the outer surface of the catheter via small capillary-like apertures which are defined in and through and, optionally, distributed along the outer surface of the outer tube. The apertures are predeterminately sized so that when the first fluid is delivered outwardly from the channel through the capillary apertures, it adheres to and coats the exterior peripheral surface of that portion of the outer tube which extends within the body, thereby creating an effective anti-infection barrier along the exterior surface of the second tube. In this manner the risk of infection along the exterior surface of the catheter while it is positioned in situ within the body is significantly reduced.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote similar elements throughout the several views:

FIG. 2 is an enlarged, cross-sectional side view similar to FIG. 1 and depicting that portion of the catheter device that is inserted into the body and the coating action of the first (e.g. anti-microbial) fluid;

FIG. 3 is a cross-sectional view taken along the lines 3—3 in FIG. 1;

FIGS. 5 and 6 depict alternate configurations and locations of the capillary apertures defined in and through the outer tube of the inventive catheter.

DETAILED DESCRIPTION OF THE PREFERRED EMBODIMENTS

Figure 4:
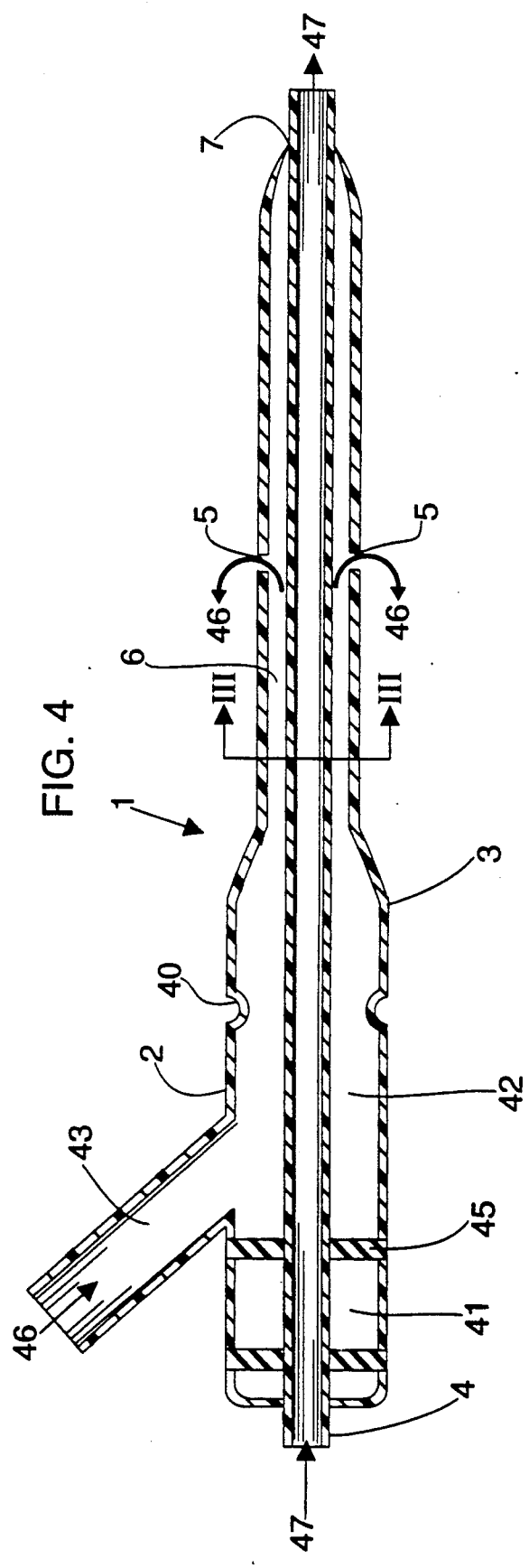
FIG. 4 is a cross-sectional side view of the catheter of FIG. 1 depicting the relationship of the inner and outer tubes and the formation of the annular fluid communication channel therebetween.

With initial reference to FIG. 4 which illustrates a cutaway side view of a catheter-type intravascular device 1 constructed in accordance with the present invention, the device 1 includes a first or outer tube 3. Positioned within and in longitudinally coaxial relation to outer tube 3 lies a second or inner tube 4. The outer diameter of the second tube 4 is smaller than the inner diameter of outer tube 3, thereby forming a coaxially annular channel 6 in the space between the two tubes. Outer tube 3 terminates in an opening 7 through which the second tube 4 extends. The first tube 3 is narrowed or tapered in the region of the opening 7 whereby the first tube 3 sealingly engages the second tube 4, creating a fluid barrier which effectively closes and terminates the channel 6. The channel 6 forms a fluid communication path 46 for a first fluid whereas the second tube 4 forms a second fluid communication path 47 for a second fluid. Positioned along and through the outer surface of the first tube 3 are a plurality of small capillary apertures 5. These apertures are in direct fluid communication with the channel 6, thereby enabling a first fluid 10 to be delivered outwardly from the channel 6 to and onto the outer surface of the first tube 3. The coaxial relationship of the first and second tubes, and the formation of the coaxially annular fluid communication channel 6 defined between the first and second tubes, are shown in detail in the sectional view of FIG. 3.

Also depicted in FIG. 4 is a hub unit 2 which provides a mechanism for connecting the first tube 3 and the second tube 4 to external apparatus for delivery of the first and second fluids. The hub unit comprises a central region divided into a first branch 41 and a second branch 42. The second branch 42 is in fluid communication with a third branch 43 which extends at an angle away from the first and second branches. Within the first branch 41 are seals 45 which sealingly engage the second tube 4 when the second tube 4 is positioned within the hub 2. Seal 45 engages the second tube 4 to create a fluid tight barrier whereby the second branch 42 and third branch 43 form a continuous fluid communication path that leads to the fluid communication channel 6 formed in the coaxial clearance or space between the outer face of the second tube 4 and the inner periphery or face of the first tube 3. The first fluid communication path 46 permits delivery of first fluid from an external apparatus connected to the third branch 43, through the second branch 42, further through the channel 6, and out through the capillary apertures 5. Additionally illustrated in FIG. 4 is a groove 40 which extends circumferentially around the outside surface of the hub 2. The groove 40 provides a retaining means for a skin-engaging suture (not shown) which may be used to secure the hub to the surface of the skin and thereby maintain precise relative positioning of the inventive device while its tubes 3, 4 are inserted through the skin and into a blood vessel.

Figure 1:
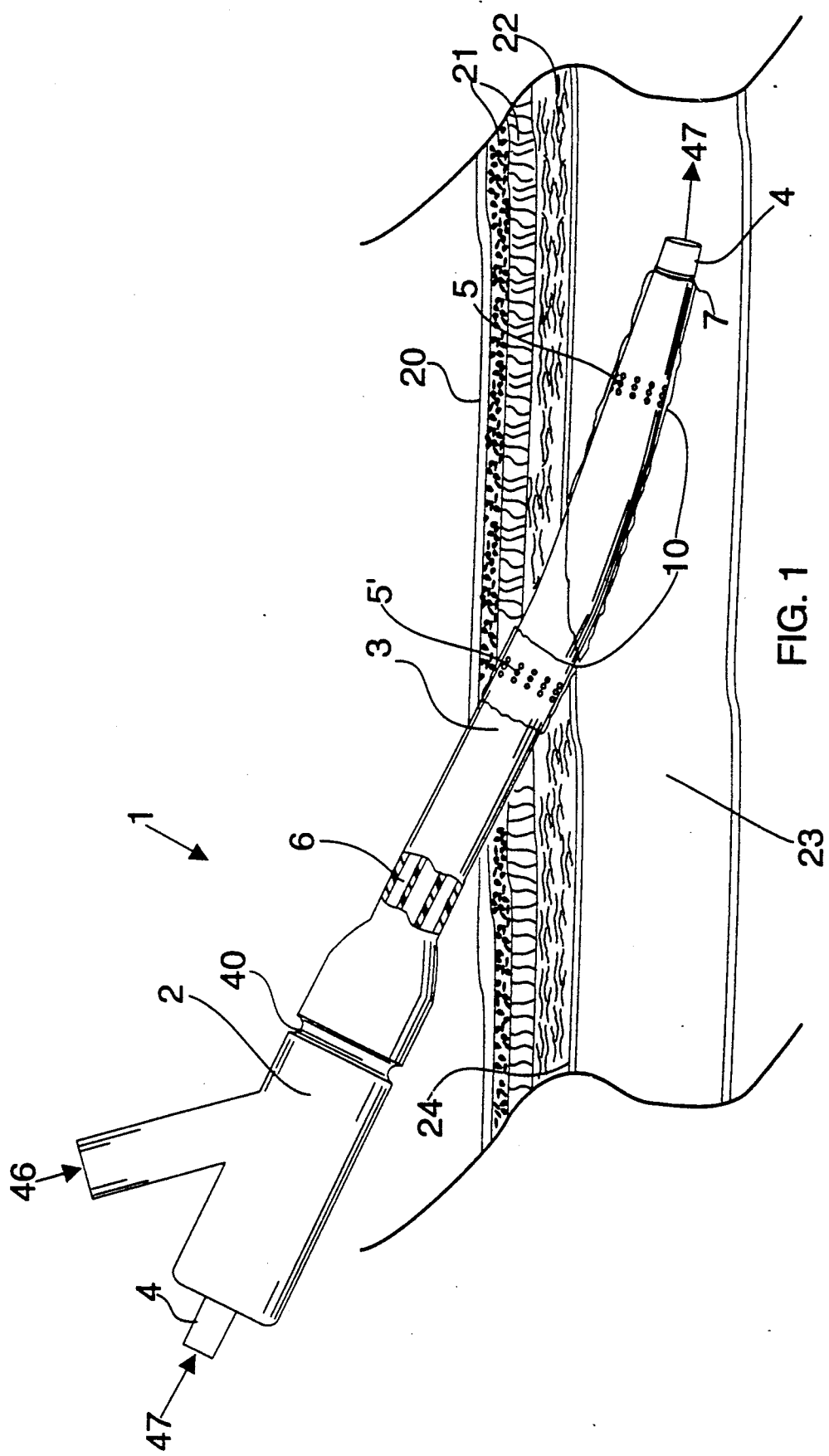
FIG. 1 is a side view, partly in cross-section, of a catheter constructed in accordance with the present invention and shown in operative position extending through the skin and body tissue and into a blood vessel.

FIG. 1 shows the catheter-type intravascular device 1 of the invention in use and, more particularly, operatively inserted into a blood vessel 23. As there shown, the device 1 is extended through the skin surface 20, through the layers of skin 21 surrounding the blood vessel, through the surrounding tissue 22 about or proximate the blood vessel, and through the blood vessel wall 24. The first and second tubes 3, 4 are assembled such that the second tube 4 is positioned within the first tube 3, and the second tube 3 is then extended into the blood vessel 23 through an opening 7 in the distal end of the first tube 3. The longitudinally coaxial relationship of the first and second tubes defines the coaxially annular fluid communication channel 6 in the space or clearance between the two tubes and thereby forms the fluid communication path 46 for the first fluid 10. The second tube 4 forms the second fluid communication path 47 for the second fluid. The first and second tubes are preferably capable of longitudinal movement relative to each other, thereby permitting precise positioning of the tubes within the body and, in suitable applications, to provide for selective replacement of the second tube 4 while the first tube 3 remains positioned in the blood vessel.

In one currently contemplated mode of use, the fist tube 3 is inserted through the skin and into the blood vessel, and is there properly positioned, and the second tube 4 is then inserted through the first tube thereby also positioning the second tube in the blood vessel. After positioning the tubes 3, 4, two fluid paths are formed for fluid communication with the blood vessel. The second tube 4 is used in the manner of any standard catheter, either feeding or infusing fluids into or withdrawing fluids from the blood vessel. The first tube 3, however, is used to deliver an anti-infective agent into the channel 6 and outwardly through the capillary apertures 5 and 5' which are positioned along and through the first tube 3. The predeterminately sized capillary apertures 5, 5' may, for example, be formed as small circular openings as shown in FIG. 2, said predetermined size of said capillary aperture being selected for predeterminately controlling the flow of the first fluid through said aperture so that as the first fluid is delivered outwardly from said channel through said aperture, the first fluid remains substantially on and along the outer peripheral surface of said first tube proximate its distal end portion so as to coat said distal end portion of the first tube with the first fluid and thereby create an anti-infective barrier on and along the first tube outer peripheral surface disposed within the body. Each circular opening is sized small enough to release the first fluid in a capillary-like fashion. That is, the fluid moves through the small opening and continues out and along the outer surface of the tube, instead of being ejected outward and away from the tube, so that when the first fluid 10 is delivered from the channel 6 through the apertures 5, 5' the fluid 10 remains on and along and adheres to and coats the outer surface of the first tube 3. The principle by which this coating action occurs is known in the art, and results from a tendency of fluids ejected through sufficiently small openings to form individual bubbles which coalesce, adhere to and coat the outer surface of a tube from which the fluid is discharged. This coating acts as an anti-infective barrier, greatly inhibiting the growth of infectious organisms along the surface of the inserted device. The first fluid 10 may be a medicament fluid selected from any of a number of commonly used anti-infective or anti-microbial agents such as, for example, a non-specific, anti-microbial organic short chain fatty acid. The second tube 4 provides a fluid communication path 47 for a second fluid to be delivered into the blood stream in a conventional manner known and used in traditional catheters.

FIG. 2 depicts the inventive device 1 in use and operatively inserted into a blood vessel 23, and shows in greater detail the skin layers 21 and tissue layer 22 surrounding the blood vessel 23. It also shows the 3 regions into which the device 1 can, for ease of description and discussion, be separated. The first region is the first tube distal end first region 25. This is the region which remains within the interior of the blood vessel while the device 1 is inserted. The second region is the first tube distal end second region 26. This is the region which extends proximally (i.e. upwardly in FIG. 2) from the wall of the blood vessel 24 but remaining beneath (or at least not extending outwardly beyond) the surface of the skin 20. The third and final region is the first tube proximal region 27 which extends beyond and outside of the skin surface 20. The capillary apertures 5 are distributed along the outer surface of the first tube distal end first region 25. When the first fluid 10 is caused to flow through the channel 6 and out through the capillary apertures 5, the first fluid 10 will coat the outer surface of the first tube along at least the first tube distal end first region 25. In this way an anti-infective barrier is caused to form along the outer surface of the first tube distal end first region 25, thus inhibiting the growth of infectious agents or the like or infection along that portion of the device 1 which lies within the blood vessel 23.

The first fluid 10 may also be caused to flow through the channel 6 and outward through capillary apertures 5', thus causing the first fluid 10 to additionally or alternatively form a coating along the outer surface of the first tube distal end second region 26. This effectively forms an anti-infective barrier in the region which starts proximate the blood vessel wall 24 and which ends at or beneath the skin surface 20. In this way an anti-infective barrier may be created along the outer surface of the device 1 as it extends through the skin layers 21 and the surrounding tissue 22 around the blood vessel 23.

As can be seen from the foregoing, the first fluid may be delivered so as to coat substantially the entire outer surface of the device which is disposed beneath the surface of the skin and within a blood vessel, thereby greatly reducing the risk of infection both within the blood vessel and, in addition, in the skin and tissue immediately surrounding the blood vessel. The device may be configured so as to provide the capillary apertures only in the first tube distal end first region 25 as denoted by the apertures 5, or solely in the first tube distal end second region 26, as indicated by the apertures 5', or in both regions simultaneously. The choice will depend, at least in part, on the criticality and other aspects of the application to which the device is applied, as well as on any particular anti-infective measures otherwise required.

FIG. 5 depicts an alternative configuration for the capillary apertures. As seen by way of example in FIG. 5, the capillary apertures may be shaped as elongated, longitudinally disposed slits 50 which are distributed along the outer surface of the first tube 3. These elongated, longitudinally disposed slits must, in accordance with the invention, be predeterminately sized so as to create the previously mentioned coalescence of the first fluid 10 along the outer surface of the first tube 3 as the first fluid is discharged from the fluid communication path 46.

FIG. 6 illustrates a further alternative configuration for the capillary apertures. In FIG. 6, the capillary apertures are shown as elongated slits 60 oriented transverse to the longitudinal axis of the first tube 3. These elongated transverse slits 60 must, once again, be predeterminately sized so as to create the previously mentioned coalescence of the anti-infective first fluid 10 along the outer surface of the first tube 3.

As will now be apparent from the foregoing description and associated drawings, the inventive device serves the traditional function of an intravenous catheter whereby a second fluid may be introduced into the blood stream through the second fluid communication path 47 from an external apparatus. By additionally providing a first fluid communication path 46 through which an anti-infective agent is deliverable via the channel 6 and the apertures 5, 5', a prophylactic coating may be formed along the outside surface of the catheter as it is inserted and while it remains in situ beneath the surface of the skin and within the blood vessel, thereby allowing it to be left in place for extended periods of time without the risk of infection currently associated with such inserted devices. It should also be recognized that the second tube 4 can be removed and replaced or reinserted while the first tube remains in place, without the necessity of removing the first tube. This provides the additional flexibility of modifying or changing the characteristics of the second fluid communication path 47, and allows delivery of alternate second fluids through the second tube along the second fluid communication path 47.

It should be further noted that the shape and diameter of the individual tubes are generally functions of design choice and/or of the application to which the intravascular device will be applied, and the constructions illustrated and described herein are not intended to limit the functionality of the device with respect to its anti-infective properties.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, however, therefore, to be limited only as indicated by the scope of the claims appended hereto.

What is claimed is:

1. A catheter insertable into a body for establishing an intravascular fluid communication path between a location external to the body and a blood vessel within the body and surrounded by body tissue, said catheter comprising:

a first elongated tube capable of penetrating the body tissue surrounding a blood vessel and a wall of the blood vessel, said first tube having an outer peripheral surface, a distal end portion operatively insertable into the body, a proximal end portion operatively disposed outside of the body, and an opening defined at said distal end portion, said distal end portion having a first tube distal first region which extends distally from a point proximate the blood vessel wall and into the blood vessel, and a first tube distal end second region which extends proximally from said point proximate the blood vessel wall and through the body tissue surrounding the blood vessel;

a second elongated tube disposed longitudinally within said first tube, said second tube having a distal end portion insertable into the blood vessel through said first tube distal end opening, said first tube distal end opening being sized so as to fluid-tightly sealingly engage said second tube, said first and second tubes defining therebetween a coaxial channel extending longitudinally along and within said first tube as a first fluid communication path through which a first fluid effective for retarding infection is deliverable, and said second tube defining therewithin a second fluid communication path through and along which a second fluid is flowable between a location external to the body and the blood vessel;

said distal end of said second tube extending outwardly beyond the distal end of said first tube and said first and second tubes being longitudinally movable relative to each other for selective adjustment of the extension of said second tube outwardly beyond said first tube distal end through said first tube distal end opening; and said first tube having a predeterminately-sized capillary aperture defined in at least one of said first tube distal end first region and said first tube distal end second region for delivering the first fluid outwardly from said channel, said predetermined size of said capillary aperture being selected for predeterminately controlling the flow of the first fluid through said aperture so that as the first fluid is delivered outwardly from said channel through said aperture, the first fluid remains substantially on and along the outer peripheral surface of said first tube proximate its distal end portion so as to coat said distal end portion of the first tube with the first fluid and thereby create an anti-infective barrier on and along the first tube outer peripheral surface disposed within the body.

2. The catheter according to claim 1 wherein said predeterminately-sized capillary aperture comprises a first predeterminately-sized capillary aperture defined in said first tube distal end first region and a second predeterminately-sized capillary aperture defined in said first tube distal end second region.

3. The catheter according to claim 1, further comprising a plurality of said predeterminately-sized capillary apertures defined in at least one of said first tube distal end first region and said first tube distal end second region.

4. The catheter according to claim 1, further comprising a plurality of said predeterminately-sized capillary apertures defined in said first tube distal end first region and in said first tube distal end second region.

5. The catheter according to claim 1, wherein said capillary aperture is substantially circular in cross-section.

6. The catheter according to claim 1, wherein said capillary aperture is shaped as an elongated slit oriented substantially along to the longitudinal axis of said first tube.

7. The catheter according to claim 1, wherein said capillary aperture is shaped as an elongated slit oriented at an angle transverse to the longitudinal axis of said first tube.

8. The catheter according to claim 3, wherein said plural capillary apertures are distributed circumferentially along the outer surface of the distal end portion of said first tube.

9. The catheter according to claim 4, wherein said plural capillary apertures are distributed circumferentially along the outer surface of the distal end portion of said first tube.

10. The catheter according to claim 1, wherein the first fluid is a non-specific anti-microbial short chain fatty acid.

11. The catheter according to claim 1, wherein each of said first tube and said second tube is flexible.

12. In combination:
a device insertable into a body for establishing an intravascular fluid communication path between a location external to the body and a blood vessel within the body and surrounded by body tissue, said device comprising:

a catheter comprising a first elongated tube capable of penetrating the body tissue surrounding a blood vessel and a wall of the blood vessel, said first tube having an outer peripheral surface, a distal end portion operatively insertable into the body, a proximal end portion operatively disposed outside of the body, and an opening defined at said distal end portion, said distal end portion having a first tube distal end first region which extends from a point proximate the blood vessel wall and into the blood vessel, and a first tube distal end second region which extends from a point proximate the blood vessel wall and through the body tissue surrounding the blood vessel;

a second elongated tube disposed longitudinally and movable relative to said first tube, said second tube having a distal end portion insertable into the blood vessel through said first tube distal end opening, said first tube distal end opening being sized so as to fluid-tightly sealingly engage said second tube, said first and second tubes defining therebetween a coaxial channel extending longitudinally along and within said first tube as a first fluid communication path, said second tube defining therewithin a second fluid communication path through and along which a second fluid is flowable between a location external to the body and the blood vessel; and a first fluid effective for retarding infection and deliverable through said first fluid communication path and deliverable outwardly from said first fluid communication path onto the outer peripheral surface of said first tube through a predeterminately sized capillary aperture defined in at least one of said first tube distal end first region and said first tube distal end second region, said predetermined size of said capillary aperture being selected for predeterminately controlling the flow of the first fluid through said capillary aperture so that as the first fluid is delivered outwardly from said fluid communication channel through said aperture, the first fluid remains substantially on and along the outer peripheral surface of said first tube proximate its distal end portion so as to coat said distal end portion of the first tube with the first fluid and thereby create an anti-infective barrier on and along the first tube outer peripheral surface disposed within the body.

13. A method for reducing the risk of infection normally associated with establishing intravascular fluid communication between a location external to a body and a blood vessel within the body and surrounded by body tissue, comprising the steps of:

inserting, into the blood vessel, a distal end portion of an elongated first tube capable of penetrating the body tissue surrounding a blood vessel and a wall of the blood vessel and having a first tube distal end first region which extends distally from a point proximate the blood vessel wall and into the blood vessel, and a first tube distal end second region which extends proximally from said point proximate the blood vessel wall and through the body tissue surrounding the blood vessel, the first tube further including a proximal end portion operatively disposed outside the blood vessel;

inserting a distal end portion of an elongated second tube into the blood vessel by:
  slideably positioning the second tube within the first tube to create a longitudinal channel defined coaxially between the first and second tubes; and
  slidably extending the second tube within and along the first tube so that the distal end of the second tube projects through and outwardly beyond an opening defined at the distal end of the first tube and into the blood vessel to establish an intravascular fluid communication path between an external apparatus and the blood vessel through the second tube; and
delivering a fluid effective for inhibiting infection through said channel and outwardly into the body through a capillary aperture defined in at least one of said first tube distal end first region and said first tube distal end second region and predeterminately sized so that as the infection inhibiting fluid is delivered outwardly through said capillary aperture from said channel the infection inhibiting fluid remains substantially on and along the outer peripheral surface of the first tube so as to coat the first tube outer peripheral surface with the infection inhibiting fluid and thereby create an anti-infective barrier along the outer peripheral surface of the first tube within the body.

14. The method according to claim 13, wherein said step of delivering an infection inhibiting fluid comprises delivering an infection inhibiting fluid through said channel and outwardly into the body through said capillary aperture, said capillary aperture being defined in said first tube distal end first region.

15. The method according to claim 13, whereby said step of delivering an infection inhibiting fluid comprises delivering an infection inhibiting fluid through said channel and outwardly into the body through said capillary aperture, said capillary aperture being defined in the first tube distal end second region.

16. The method according to claim 13, wherein said step of delivering an infection inhibiting fluid comprises delivering an infection inhibiting fluid through said channel and outwardly into the body through a plurality of said capillary apertures defined in at least one of said first tube distal end first region and said first tube distal end second region.

17. The method according to claim 13, wherein said step of delivering an infection inhibiting fluid comprising delivering an infection inhibiting fluid through said channel and outwardly into the body through a plurality of said capillary apertures, at least one of said plurality of apertures being defined in said first tube distal end first region and at least one of said plurality of apertures being defined in said first tube distal end second region.

18. A catheter insertable into a body for establishing an intravascular fluid communication path between a location external to the body and a blood vessel within the body and surrounded by body tissue, said catheter comprising;
  a first elongated tube capable of penetrating the body tissue surrounding a blood vessel and a wall of the blood vessel, said first tube having an outer peripheral surface, a distal end portion operatively insertable into the body, a proximal end portion operatively disposed outside of the body, and an opening defined at said distal end portion, said distal end portion having a first tube distal first region which extends distally from a point proximate the blood vessel wall and into the blood vessel, and a first tube distal end second region which extends proximally from said point proximate the blood vessel wall and through the body tissue surrounding the blood vessel;
  a second elongated tube disposed longitudinally within said first tube, said second tube having a distal end portion insertable into the blood vessel through said first tube distal end opening, said first tube distal end opening being sized so as to fluidtightly sealingly engage said second tube, said first and second tubes defining therebetween a channel extending longitudinally along and within said first tube as a first fluid communication path through which a first fluid effective for retarding infection is deliverably, and said second tube defining therewithin a second fluid communication path through and along which a second fluid is flowable between a location external to the body and the blood vessel;
  said first tube having a predeterminately-sized capillary aperture defined in at least one of said first tube distal end first region and said first tube distal end second region for delivering the first fluid outwardly from said channel, said predetermined size of said capillary aperture being selected for predeterminately controlling the flow of the first fluid through said aperture so that as the first fluid is delivered outwardly from said channel through said aperture, the first fluid remains substantially on and along the outer peripheral surface of said first tube proximate its distal end portion so as to coat said distal end portion of the first tube with the first fluid and thereby create an anti-infective barrier on and along the first tube outer peripheral surface disposed within the body;
  means on said first tube for connecting said first tube to an external apparatus for delivery of the first fluid distally through said channel and through said capillary aperture for discharge onto the outer surface of said first tube, said means comprising a hub; and
  said hub having a first hollow portion through which said second tube passes, said first hollow portion being operatively connected to the proximal end of said first tube and including at least one fluid-tight seal, said seal engaging said second tube and dividing said first hollow portion into a first branch and a second branch, said second branch being in fluid communication with said channel, and a second hollow portion defining a third branch, said third branch being in fluid communication with and extending at an angle from said second branch for establishing a third fluid communication path between said hub and said channel to enable delivery of first fluid from a point outside of the body, through said hub and into said channel.

19. The catheter according to claim 12, wherein said hub further comprises at least one groove extending along an outside peripheral surface of said hub, said groove being aligned in transverse relation to the longitudinal axis of said channel, said groove having a depth selected so that a suture attached to the body may be retained in said groove for securing said hub to the body.

* * * * *